(12) United States Patent
Liberman

(10) Patent No.: US 6,679,070 B1
(45) Date of Patent: Jan. 20, 2004

(54) METHOD FOR IDENTIFYING THAWED AND REFROZEN PRODUCTS

(75) Inventor: Barnet Liberman, NY, NY (US)

(73) Assignee: Winterlab, New York, NY (US)

( * ) Notice: Subject to any disclaimer, the term of this patent is extended or adjusted under 35 U.S.C. 154(b) by 0 days.

(21) Appl. No.: 10/231,234

(22) Filed: Aug. 29, 2002

(51) Int. Cl.$^7$ ............................................. F25B 49/00
(52) U.S. Cl. ................................... 62/125; 116/207
(58) Field of Search .................. 62/125, 129; 116/207, 116/216; 374/102, 106, 162

(56) References Cited

U.S. PATENT DOCUMENTS

| | | | |
|---|---|---|---|
| 3,177,843 A | 4/1965 | Geocaris ................. | 116/114.5 |
| 3,220,259 A | 11/1965 | Beyer ......................... | 73/358 |
| 3,696,679 A * | 10/1972 | Peterson et al. ............ | 340/590 |
| 3,701,282 A | 10/1972 | Peterson ...................... | 73/358 |
| 3,967,579 A | 7/1976 | Seiter ...................... | 116/114.5 |
| 4,022,149 A | 5/1977 | Berger ......................... | 116/114.5 |
| 4,064,828 A * | 12/1977 | Clark ......................... | 116/215 |
| 4,114,443 A | 9/1978 | Clark ......................... | 73/358 |
| 4,145,918 A | 3/1979 | Couch et al. ............... | 116/216 |
| 4,148,748 A | 4/1979 | Hanlon et al. .............. | 252/408 |
| 4,309,185 A * | 1/1982 | Simon et al. ................ | 436/21 |
| 4,601,909 A | 7/1986 | Nagoshi ..................... | 426/524 |
| 4,654,217 A | 3/1987 | Nagoshi ..................... | 426/524 |
| 4,657,768 A | 4/1987 | Nagoshi ..................... | 426/524 |
| 4,689,963 A | 9/1987 | Sakai ............................ | 62/64 |
| 4,743,343 A | 5/1988 | Sakai ......................... | 203/22 |
| 4,840,034 A | 6/1989 | Liberman ..................... | 62/64 |
| 4,893,477 A | 1/1990 | Vazquez ...................... | 62/125 |
| 5,001,047 A | 3/1991 | Liberman ....................... | 435/1 |
| 5,034,233 A | 7/1991 | McCloy, Jr. ................. | 426/87 |
| 5,102,233 A | 4/1992 | Staerk et al. ............... | 374/160 |
| 5,267,794 A | 12/1993 | Holzer ....................... | 374/160 |
| 5,301,632 A * | 4/1994 | Cayol et al. ................ | 116/217 |
| 5,490,476 A | 2/1996 | Veitch et al. ............... | 116/217 |
| 5,695,284 A * | 12/1997 | Waters ....................... | 374/162 |
| 5,997,927 A | 12/1999 | Gics .......................... | 426/383 |
| 6,029,601 A | 2/2000 | Suya .......................... | 116/217 |
| 6,038,870 A | 3/2000 | Tiby .......................... | 62/129 |
| 6,156,366 A * | 12/2000 | Waldstr.o slashed.m et al. . | 426/515 |
| 6,357,383 B1 * | 3/2002 | Al harshani ................. | 116/216 |
| 6,451,364 B1 * | 9/2002 | Ito .............................. | 426/244 |

FOREIGN PATENT DOCUMENTS

| | | | |
|---|---|---|---|
| GB | 2215460 | | 9/1989 |
| JP | 60075860 A | * | 4/1985 |
| WO | WOn98/02722 | * | 1/1998 |

OTHER PUBLICATIONS

U. S. patent application Publication, Pb. No. : US 2002/0106443 A1, date Aug. 8, 2002.*

* cited by examiner

Primary Examiner—William E. Tapolcai
Assistant Examiner—Mohammad M. Ali
(74) Attorney, Agent, or Firm—Cohen, Pontani, Lieberman & Pavane

(57) ABSTRACT

A method of freezing a food product comprises the step of forming an indentation on the frozen food product. Such indentation is capable of being irreversibly altered after the frozen food product is thawed so that it is an indication that the frozen food product has been thawed during storage.

25 Claims, 2 Drawing Sheets

METHOD FOR IDENTIFYING THAWED AND REFROZEN PRODUCTS

BACKGROUND OF THE INVENTION

1. Field of the Invention

The present invention relates to a method of identifying food stuffs that are thawed and later refrozen. More specifically, the thawed and refrozen food stuffs are identified by the change of their physical appearance.

2. Description of the Related Art

Many food stuffs must be stored in continuously frozen condition to maintain their taste and quality. However, it is not uncommon that such frozen food stuffs are temporarily defrosted or thawed due to changes of the storage conditions, such as temperature change or changes of other environmental factors, and then they are refrozen when the storage conditions resume. Thawing or defrosting, even for a short period of time, may encourage the growth of bacteria or damage cell structures, which result in deterioration, spoilage and unfavorable odors and tastes. Sometimes, such adversely affected food stuffs are unfit for human consumption. Subsequent refreezing of the products usually will not remove such undesirable characteristics caused by thawing or defrosting.

While the thawed and refrozen food products may have lost their freshness, consumers or users of such food products usually are unable to determine whether such food products have been adversely affected by thawing or defrosting from their appearance.

Many devices and methods associated with such devices have been developed to indicate the thawing and defrosting process occurring during storage as a result of the changes of the storage conditions. Typically, these devices include a material which irreversibly changes its color, shape or other properties at or above a pre selected temperature such that such irreversible changes can be visualized.

U.S. Pat. No. 4,022,149 describes a thaw indicator, which comprises a capsule formed from an edible wax and filled by a mixture of edible gelatin and a colored liquid. The capsule is surrounded by a non-toxic blotter like absorbent material which is coextensive and in contact with at least a substantial portion of the outer surface. When the thaw indicator is frozen, along with the package, the mixture of gelatin and colored liquid expands enough so it cracks the edible wax capsule. While the mixture of gelatin and colored liquid is frozen, it can not be absorbed by the blotter-like absorbent material. When the temperature of the package rises above the pre-determined level for a predetermined period of time, the mixture melts and colored mixture is absorbed by the blotter-like material, staining it and providing a non-reversible indication that the contents of the package has been thawed or defrosted.

U.S. Pat. No. 4,114,443 teaches a freeze/thaw indicator having a container which comprises an upper transparent portion and a lower opaque portion provided with inward projections. Colored water can be frozen in place within the opaque portion. The projections hold the ice in place in the opaque portion of the container so that the extent of thawing is evidenced by the presence of water in the transparent portion of the container in the event of a rise in temperature in the freezer compartment.

U.S. Pat. No. 5,301,632 teaches a thaw indicator comprising a case or envelope, which is sealed in an inviolable manner and, in the case or envelope, a meltable object having a predetermined shape different from the internal shape of the case, this object has a melting point below or equal to the thawing or keeping temperature, of the product. The case is also partially transparent so that the meltable object can be seen through the transparent portion. Once the object melts, the original shape is irreversibly changed.

U.K. Patent Application Number G.B 2215460A describes a thaw indicator consists of a simple ice cube which is made from a mildly dyed water solution, placed in a clear plastic bag. The bag is then sealed and fitted into foodstuff packaging. The ice cube changes its shape if it melts.

All of the above described thaw indicators are made separately from the frozen products and can be easily removed from the package and replaced with a new one. In addition, most of these thaw indicators are not reusable and they usually have to be obtained from else where, which inevitably becomes too costly and inconvenient. Further, an indicator that is made in a material different from the frozen food product and placed separately from the frozen food product might not accurately reflect the actual frozen/thawed state of the frozen food product.

SUMMARY OF THE INVENTION

Accordingly, an object of the present invention is to provide a simple method identifying thawed and refrozen food products by the frozen food product itself, not by a separate indicator unrelated to the frozen food product.

Another object of the present invention is to provide a method of freezing a food product in connection with a mold where the food product is placed prior to the freezing process. The mold includes an inward projection that is capable of creating an indentation or a mark or a void on the food product in such a way that the indentation or the mark or the void cannot return to its original shape or condition after the frozen food product is thawed.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Food products encompassed by the present invention include any food stuffs, whether liquid or solid, that is flexible enough to be reshaped or reconfigured, including but not limited to, protein products such as a reconstituted meat product from trims of fish, beef, pork or chicken, fish roes such as caviar, and vegetable products.

Figure 1:
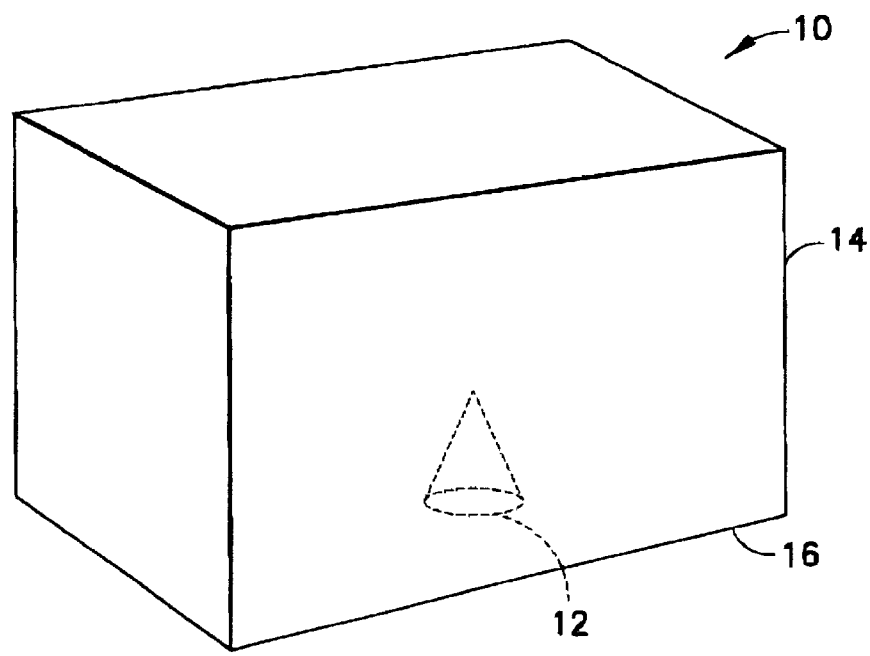
FIG. 1 shows a mold with an inward projection in a cone shape.
Figure 2:
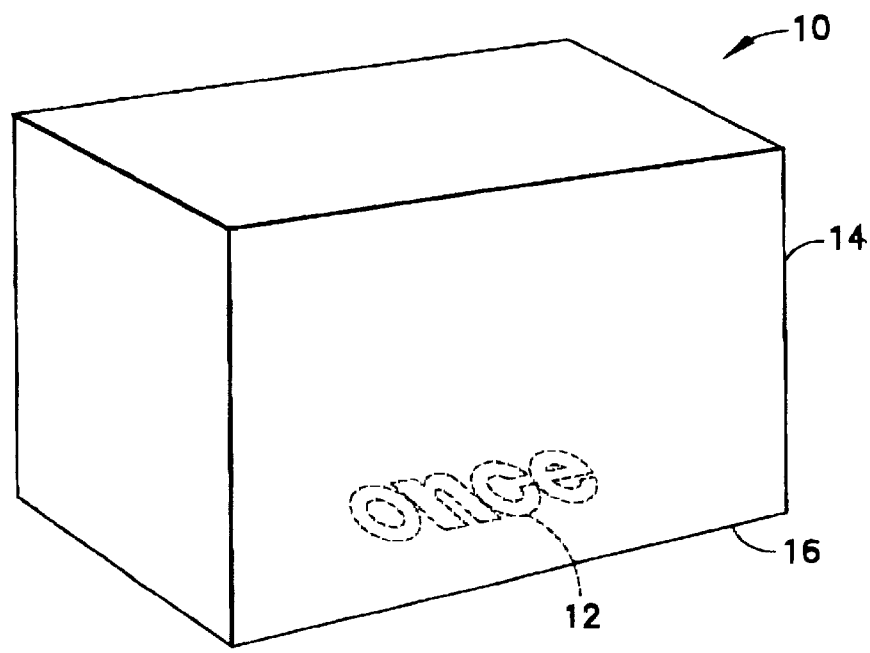
FIG. 2 shows a mold with an inward projection in a word shape.

Referring now to FIG. 1, a mold 10 comprises a bottom 16 and a wall 14 extending perpendicularly from the bottom. The mold 10 is left open on the side opposite to the bottom so that one can conveniently put any food products in and out of the mold. Mold 10 may be designed, in terms of shape and dimension, to suit the food product to be frozen. Preferably, Mold 10 is made in dimensions comparably to the dimensions of the food product. A projection 12 extends inwardly at bottom 16. Projection 12 may shaped in any geometric form such as a rectangular solid, a cone, a cylinder, a pyramid or the like. The dimensions of the projection 12 should be proportional to the size of the food product, as can be determined readily by a person of ordinary skill in the art. A suitable projection should have a shape and dimensions that are sensitive to the elevation of the surrounding temperature. The height of projection 12, although not critical, is preferably about one to three centimeters. Alternatively, projection 12 may be shaped in the form of a letter, a word, a number, a date, an icon or the like, as shown in FIG. 2.

Figure 3:
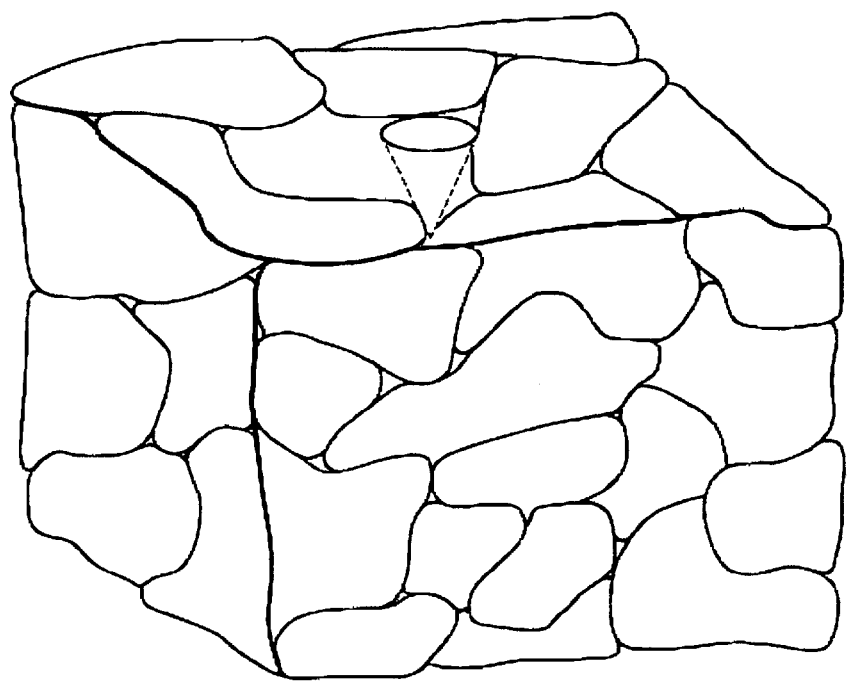
FIG. 3 shows an indentation on a frozen food product.

Before a food product is subject to a freezing process, it is first placed in mold 10 in such a way that it completely covers projection 12. After the food product is placed in mold 10, a pressure may be exerted on the food product in the mold so as to ensure that no space is left between the food product and the surface of the projection 12. As a result, the projection 12 creates an indentation complimentary to the shape of projection 12 on the food product, as shown in FIG. 3.

The food product in mold 10 is then subject to a freezing process, which may be accomplished by means of a blast freezer or any other conventional freezer, preferably, the food products are frozen using the "cooled-brine methods" (TruFresh®) disclosed in U.S. Pat. Nos. 4,601,909; 4,654,217; 4,657,768; 4,689,963; 4,743,343; 4,840,034; 4,840,035 and 5,001,047, the contents of which patents are incorporated herein by reference in their entireties. As described therein, these cooled-brine methods, unlike conventional freezing methods, advantageously maintain the freshness or tastiness of the meat by maintaining maximum cellular integrity of the meat tissue and minimizing the number of ruptured cells during the freezing process. As used hereinafter, the term "TRUEFRESH freezing process" means the freezing process described in U.S. Pat. Nos. 4,601,909; 4,654,217; 4,657,768; 4,689,963; 4,743,343; 4,840,034; 4,840,035 and 5,001,047.

Although brine solutions of various compositions, as disclosed in the aforementioned cooled-brine method patents may be used, at least about 0.005% by weight of cruciferous oil is preferably included in the brine. Preferably, about 0.005% to 0.018% by weight of cruciferous oil such as rapeseed oil should be used. Alternatively, the amount of cruciferous oil may be selected such that a maximum amount of the oil is dissolved in the brine. Presently preferred brine composition include, by weight, bout 43.18% water, about 44.06% propylene glycol, about 12.75% calcium chloride, and about 0.01% rapesed oil. The temperature of the brine should be between about −22.degree. and −46.degree. F., and preferably between about 37.degree. and −41.degree. F.

After the freezing process is completed, the food product is removed from the mold. An indentation on the frozen food product resulting from the projection 12 is then revealed and such indented frozen food product is then ready to be packaged.

The frozen food product carrying the indentation is to be packaged in a container, which is at least partially transparent, such as a plastic bag, a glass jar or a box with a window, so as to enable the indentation to be visualized.

Figure 4:
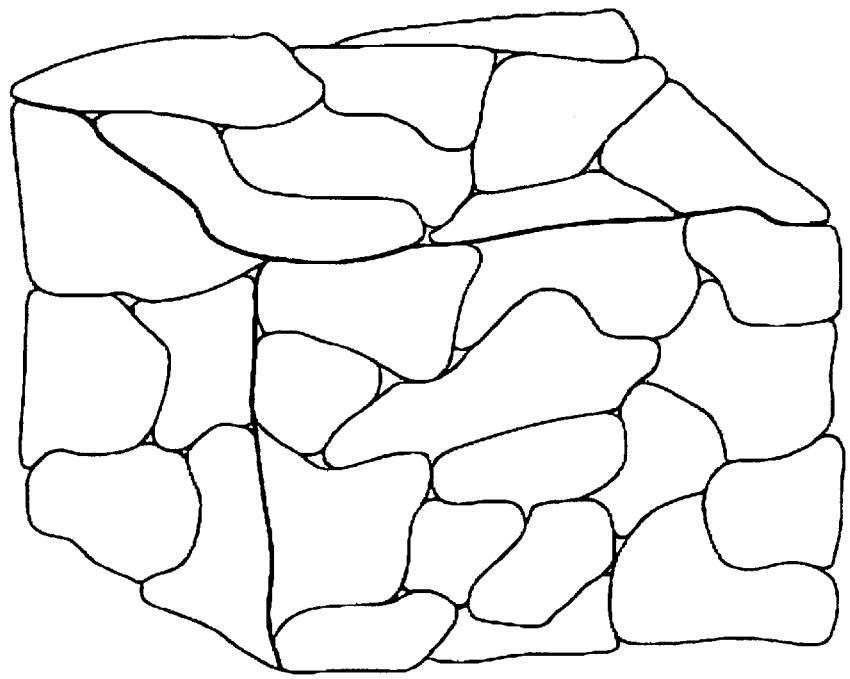
FIG. 4 shows disappearance of the indentation after the frozen food product is thawed.

The indentation created in the frozen food product as described above will not disappear or be deformed during the storage so long as such frozen food product continues to stay in its frozen state. When rise of temperature or change of other environmental factors results in thawing or defrosting of such frozen food product, the indentation on the frozen product will be irreversibly altered or completely disappear, as shown in FIG. 4. Refreezing the thawed or defrosted food product can not reproduce the original indentation absent the mold 10. Thus, the alteration or disappearance of the indentation on the frozen food product gives rise to an awareness that a thawing or defrosting process occurred during the storage.

EXAMPLE

A suitable amount of fish roes, such as salmon roes or caviar, are placed in a mold having a protrusion in the form of the top ¼ inch of a thimble. The fish roes together with the mold are frozen with TRUFRESH freezing process. The frozen fish roes are then removed from the mold and at that point a dimple (indentation) is formed. Then the frozen fish roes with the indentation are placed in a glass jar so that the indentation is visible. The absence of such indentation indicates that the fish roes in the jar have been thawed.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

I claim:

1. A method for freezing a food product, comprising the step of forming an indentation in said food product and freezing said food product to form a frozen food product having said indentation, said indentation being self maintained when said food product remains frozen and irreversibly altered after said food product is thawed.

2. The method of claim 1, wherein said indentation comprises an alphabet letter.

3. The method of claim 1, wherein said indentation comprises a numeral number.

4. The method of claim 1, wherein said indentation comprises an icon.

5. The method of claim 1, wherein said indentation is in an geometric shape selected from the group consisting of a rectangular solid, a cone, a cylinder and a pyramid.

6. The method of claim 1, wherein said frozen food product is fish roes.

7. The method of claim 1, wherein said frozen food product is a meat product.

8. The method of claim 1, wherein said frozen food product is a vegetable product.

9. The method of claim 1, further comprising the steps of placing a food product in a mold which comprises a projection extending inwardly on the wall of said mold, said projection is complimentary to said indentation; and freezing said food product in said mold.

10. The method of claim 9, wherein said food product is frozen by TRUFRESH freezing process.

11. The method of claim 9, further comprising the step of removing said frozen food product from said mold.

12. The method of claim 11, further comprising the step of placing said frozen food product in a partially transparent container.

13. A method of freezing a food product, comprising the steps of:
  a. placing said food product in a mold having a projection extending inwardly so as to form an indentation complimentary to said projection in said food product;
  b. freezing said food product; and
  c. removing said food product from said mold to form a frozen food product having said indentation, said indentation being self maintained when said food product remains frozen and irreversibly self altered after said food product is thawed; and
  d. placing said frozen food product in a partially transparent container.

14. The method of claim 13, wherein said food product is frozen by TRUFRESH freezing process.

15. The method of claim 13, wherein said projection comprises an alphabet letter.

16. The method of claim 13, wherein said projection comprises a numeral number.

17. The method of claim 13, wherein said projection comprises an icon.

18. The method of claim 13, wherein said frozen food product is fish roes.

19. The method of claim 13, wherein said frozen food product is meat product.

20. The method of claim 13, wherein said frozen food product is a vegetable product.

21. A frozen food product, comprising an indentation created to function as a thawing indicator which is self maintained when said food product remains frozen and irreversibly self altered after said frozen food product is thawed.

22. The method of claim 21, wherein said indentation comprises an alphabet letter.

23. The method of claim 21, wherein said indentation comprises a numeral number.

24. The method of claim 21, wherein said indentation comprises an icon.

25. The method of claim 21, wherein said indentation is in an geometric shape selected from the group consisting of a rectangular solid, a cone, a cylinder and a pyramid.

* * * * *